United States Patent
Strohl

(10) Patent No.: US 10,946,195 B2
(45) Date of Patent: Mar. 16, 2021

(54) SYSTEM AND METHOD FOR ENSURING AIRWAY PATENCY WHEN ASLEEP

(71) Applicant: Case Western Reserve University, Cleveland, OH (US)

(72) Inventor: Kingman P. Strohl, Cleveland, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 0 days.

(21) Appl. No.: 15/553,223

(22) PCT Filed: Mar. 14, 2016

(86) PCT No.: PCT/US2016/022275
§ 371 (c)(1),
(2) Date: Aug. 24, 2017

(87) PCT Pub. No.: WO2016/149176
PCT Pub. Date: Sep. 22, 2016

(65) Prior Publication Data
US 2018/0015281 A1    Jan. 18, 2018

Related U.S. Application Data

(60) Provisional application No. 62/132,727, filed on Mar. 13, 2015.

(51) Int. Cl.
*A61N 1/36* (2006.01)
*A61N 1/04* (2006.01)
(Continued)

(52) U.S. Cl.
CPC ........ *A61N 1/3601* (2013.01); *A61N 1/0492* (2013.01); *A61N 1/0502* (2013.01);
(Continued)

(58) Field of Classification Search
CPC .............. A61N 1/36014; A61N 1/3611; A61N 1/36057; A61N 1/04; A61M 2021/0005; A61M 21/00; A61B 5/4818; A61B 5/4815
See application file for complete search history.

(56) References Cited

U.S. PATENT DOCUMENTS 7,904,175 B2 *  3/2011  Scott .................... A61N 1/0517
                                                                    607/1
8,036,745 B2   10/2011  Ben-David et al.
(Continued)

FOREIGN PATENT DOCUMENTS

JP      2009233024 A  * 10/2009
WO      2011/016864 A1    2/2011
(Continued)

OTHER PUBLICATIONS

Bellemare, François, et al. "Reversibility of airflow obstruction by hypoglossus nerve stimulation in anesthetized rabbits." American journal of respiratory and critical care medicine 172.5 (2005): 606-612.
(Continued)

*Primary Examiner* — Michael W Kahelin
*Assistant Examiner* — Sana Sahand
(74) *Attorney, Agent, or Firm* — Tarolli, Sundheim, Covell & Tummino LLP

(57) ABSTRACT

One aspect of the present disclosure relates to a system that provides an alternative to traditional treatments for sleep apnea. The system allows to apply an electrical stimulus through an electrode to stimulate an afferent nerve fiber while a patient is sleeping. The system also includes activating an endogenous central nervous system (CNS)-regulated reflex response to coordinate upper airway muscles based on the stimulation of the afferent nerve fiber. Based on
(Continued)

the endogenous CNS-regulated reflex response, an airway patency in the sleeping patient can be regulated.

16 Claims, 6 Drawing Sheets

(51) Int. Cl.
 *A61N 1/05* (2006.01)
 *A61B 5/00* (2006.01)
(52) U.S. Cl.
 CPC .......... *A61N 1/0517* (2013.01); *A61N 1/3611* (2013.01); *A61N 1/36014* (2013.01); *A61N 1/36057* (2013.01); *A61B 5/4818* (2013.01); *A61N 1/0456* (2013.01)

(56) References Cited

U.S. PATENT DOCUMENTS

| | | | |
|---|---|---|---|
| 2006/0095088 A1* | 5/2006 | De Ridder | A61N 1/0529 607/48 |
| 2007/0027496 A1* | 2/2007 | Parnis | A61N 1/3601 607/42 |
| 2008/0103407 A1* | 5/2008 | Bolea | A61N 1/0556 600/529 |
| 2008/0103545 A1* | 5/2008 | Bolea | A61N 1/0556 607/42 |
| 2009/0177252 A1* | 7/2009 | Craig | A61N 1/36082 607/62 |
| 2011/0202119 A1 | 8/2011 | Ni et al. | |
| 2011/0288609 A1 | 11/2011 | Tehrani et al. | |
| 2012/0029587 A1* | 2/2012 | Zhou | A61N 1/36114 607/17 |
| 2012/0253249 A1 | 10/2012 | Wilson | |
| 2013/0197321 A1* | 8/2013 | Wilson | A61B 5/04001 600/301 |
| 2013/0245486 A1 | 9/2013 | Simon et al. | |
| 2013/0245711 A1* | 9/2013 | Simon | A61N 1/3601 607/42 |

FOREIGN PATENT DOCUMENTS

| | | | | |
|---|---|---|---|---|
| WO | WO 2011016864 A1 * | 2/2011 | ............. | A61B 5/415 |
| WO | WO-2011016864 A1 * | 2/2011 | ............. | A61B 5/415 |
| WO | WO 2013155117 A1 * | 10/2013 | ........... | A61N 1/0551 |
| WO | WO-2013155117 A1 * | 10/2013 | ........... | A61N 1/0551 |

OTHER PUBLICATIONS

Chen, Maida Lynn, et al. "Diaphragm pacers as a treatment for congenital central hypoventilation syndrome." Expert review of medical devices 2.5 (2005): 577-585.
Cherniack, N. S., et al. "Responses of upper airway, intercostal and diaphragm muscle activity to stimulation of oesophageal afferents in dogs." The Journal of physiology 349.1 (1984): 15-25.
Decker, Michael J., et al. "Functional electrical stimulation and respiration during sleep." Journal of Applied Physiology 75.3 (1993): 1053-1061.
Dempsey, Jerome A., et al. "Pathophysiology of sleep apnea." Physiological reviews 90.1 (2010): 47-112.
Dotan, Y., et al. "Parameters affecting pharyngeal response to genioglossus stimulation in sleep apnoea." European Respiratory Journal 38.2 (2011): 338-347.
Eastwood, Peter R., et al. "Treating obstructive sleep apnea with hypoglossal nerve stimulation." Sleep 34.11 (2011): 1479-1486.
Force, Adult Obstructive Sleep Apnea Task, and American Academy of Sleep Medicine. "Clinical guideline for the evaluation, management and long-term care of obstructive sleep apnea in adults." Journal of clinical sleep medicine: JCSM: official publication of the American Academy of Sleep Medicine 5.3 (2009): 263.
Germany, Robin, et al. "A novel therapeutic approach for the treatment of central sleep apnea: The remede ® system." Cardiovascular Revascularization Medicine 15.4 (2014): 235-239.
Haxhiu, Musa A., et al. "Comparison of the responses of the diaphragm and upper airway muscles to central stimulation of the sciatic nerve." Respiration physiology 58.1 (1984): 65-76.
Kezirian, Eric J., et al. "Hypoglossal nerve stimulation improves obstructive sleep apnea: 12-month outcomes." Journal of sleep research 23.1 (2014): 77-83.
Lee, Myung-Chul, et al. "Establishment of a rabbit model of obstructive sleep apnea by paralyzing the genioglossus." JAMA Otolaryngology—Head & Neck Surgery 139.8 (2013): 834-840.
Liu, Chun-yan, et al. "Effects of a mandibular advancement device on genioglossus in obstructive sleep apnoea hypopnea syndrome." European journal of orthodontics 37.3 (2014): 290-296.
Lu, Hai-yan, et al. "An animal model of obstructive sleep apnoea—hypopnea syndrome corrected by mandibular advancement device." European journal of orthodontics 37.3 (2014): 284-289.
Mustafa, Masroor, et al. "Sleep problems and the risk for sleep disorders in an outpatient veteran population." Sleep and Breathing 9.2 (2005): 57-63.
Mwenge, Gimbada B., et al. "Targeted hypoglossal neurostimulation for obstructive sleep apnoea: a 1-year pilot study." European Respiratory Journal 41.2 (2013): 360-367.
Ocasio-Tascón, Maria Elena, et al. "The veteran population: one at high risk for sleep-disordered breathing." Sleep and Breathing 10.2 (2006): 70-75.
Oliven, Arie, et al. "Effect of genioglossus contraction on pharyngeal lumen and airflow in sleep apnoea patients." European Respiratory Journal 30.4 (2007): 748-758.
Potts, Jeffrey T., Ilya A. Rybak, and Julian FR Paton. "Respiratory rhythm entrainment by somatic afferent stimulation." Journal of Neuroscience 25.8 (2005): 1965-1978.
Safiruddin, Faiza, et al. "Effect of upper-airway stimulation for obstructive sleep apnoea on airway dimensions." European Respiratory Journal 45.1 (2015): 129-138.
Schwartz, Alan R., Philip L. Smith, and Arie Oliven. "Electrical stimulation of the hypoglossal nerve: a potential therapy." Journal of Applied Physiology 116.3 (2014): 337-344.
Simon, Peggy M., et al. "Vagal feedback in the entrainment of respiration to mechanical ventilation in sleeping humans." Journal of Applied Physiology 89.2 (2000): 760-769.
Strollo Jr, Patrick J., et al. "Upper-airway stimulation for obstructive sleep apnea." New England Journal of Medicine 370.2 (2014): 139-149. APA.
Stuck, Boris A., Sarah Leitzbach, and Joachim T. Maurer. "Effects of continuous positive airway pressure on apnea—hypopnea index in obstructive sleep apnea based on long-term compliance." Sleep and Breathing 16.2 (2012): 467-471. APA.
Weaver, Edward M. "Sleep apnea devices and sleep apnea surgery should be compared on effectiveness, not efficacy." Chest 123.3 (2003): 961-962.
Woodson, B. Tucker, et al. "Randomized controlled withdrawal study of upper airway stimulation on OSA: short-and long-term effect." Otolaryngology—Head and Neck Surgery 151.5 (2014): 880-887.
PCT International Search Report and Written Opinion for corresponding PCT Application No. PCT/US2016/022275, dated Jun. 16, 2016, pp. 1-14.

* cited by examiner

SYSTEM AND METHOD FOR ENSURING AIRWAY PATENCY WHEN ASLEEP

RELATED APPLICATION

This application claims the benefit of U.S. Provisional Application No. 62/132,727, filed Mar. 13, 2015, entitled "SYSTEM AND METHOD FOR TREATING SLEEP APNEA". This provisional application is hereby incorporated by reference in its entirety for all purposes.

GOVERNMENT FUNDING

This work was supported, at least in part, by grant number 1121RX002041-01 from the Department of Veterans Affairs. The United States government may have certain rights in this invention.

TECHNICAL FIELD

The present disclosure relates generally to airway patency and, more specifically, to systems and methods for selectively activating an endogenous central nervous system (CNS)-regulated reflex responses associated with airway function to ensure airway patency during sleep.

BACKGROUND

Sleep apnea is a sleep disorder characterized by trouble breathing during sleep, which can lead to nocturnal hypoxemia and sleep fragmentation, which can lead to other co-morbidities, like daytime sleepiness. Generally, sleep apnea is to due to pauses in breathing or instances of shallow or infrequent breathing, which can be caused by a complete or partial collapse or obstruction of a patient's upper airway. Sleep apnea is poorly diagnosed and poorly treated. In fact, no drug therapies exist to treat sleep apnea. Although several mechanical therapies exist, such as continuous positive airway pressure (CPAP) therapy or a mandibular advancement device (MAD) treatment, these therapies are often improperly used, poorly tolerated, and/or ineffective. More recently, electrical stimulation of the hypoglossal nerve has emerged as an alternative to mechanical treatment when treating sleep apnea.

Hypoglossal nerve stimulation has been shown to be a safe alternative to traditional mechanical therapy. However, hypoglossal nerve stimulation has also been shown to have different efficacies for different patients. Such differences may be due to the fact that hypoglossal nerve stimulation targets a single motor nerve (CN XII), while airway patency is regulated via a portion of the central nervous system (e.g., the brainstem), which leads to the reflexive coordination of several efferent nerve-muscle units associated with upper airway muscles (e.g., the efferent nerve-muscle units can be associated with CN V, X, IX, and/or XII). Further, stimulators used for hypoglossal nerve stimulation are typically placed on or about the tongue and/or in the neck, which negatively affects a patient's speech and/or ability to swallow.

SUMMARY

The present disclosure relates generally to airway patency. Although hypoglossal nerve stimulation can provide a treatment for sleep apnea in some patients, hypoglossal nerve stimulation does not provide a standard solution for every patient due, at least in part, to the non-physiological stimulation of a single motor nerve. A more physiological solution would recognize that airway patency is regulated as a consequence of coordination of several upper airway muscles. Reflex activation of one or more of these several upper airway muscles by central nervous system (CNS)-regulated mechanisms provides a more effective and efficient alternative to hypoglossal nerve stimulation. Accordingly, the present disclosure relates, more specifically, to systems and methods for selectively activating endogenous CNS-regulated reflex responses associated with upper airway function to ensure airway patency and unobstructed breathing in a sleeping patient.

In one aspect, the present disclosure includes a method for ensuring airway patency. The method can include applying an electrical stimulus through an electrode to stimulate an afferent nerve fiber or fibers while a patient is sleeping. The method can also include activating an endogenous CNS-regulated reflex response to coordinate upper airway muscles based on the stimulation of the afferent nerve fiber. The airway patency in the sleeping patient can be regulated based on the endogenous CNS-regulated reflex response.

In another aspect, the present disclosure also includes a neural stimulation system. The system can include a signal generator programmed to generate an electrical therapy signal comprising a strength parameter, a frequency parameter, and a duration parameter sufficient to activate an endogenous CNS-regulated reflex response. The system can also include an electrode (such as a temporary electrode that can be removed after the treatment), coupled to the signal generator (e.g., internal or external), to apply the electrical therapy signal to an afferent nerve fiber of a peripheral nerve of a sleeping patient to activate the endogenous CNS-regulated reflex response to regulate airway patency in the sleeping patient. In one example, the CNS-regulated reflex can be associated with the brainstem.

In a further aspect, the present disclosure also includes another method for treating a sleeping patient to ensure airway patency. The method can include applying an electrode configuration to a patient before sleep. The electrode configuration, in some instances, can include a temporary electrode that can be placed on or into the patient's body and subsequently removed after treatment is completed. In other instances, the electrode can include a more permanent electrode, like an implantable TENS unit. The electrode configuration can coupled to a stimulator (e.g., an internal stimulator or an external stimulator), which can provide an electrical stimulus. During sleep, the electrical stimulus can be delivered through the electrode configuration to the patient to stimulate an afferent nerve fiber of a peripheral nerve. Based on the electrical stimulus, an endogenous CNS-regulated reflex can be activated to ensure that the patient's airway remains open during sleep. A response to the endogenous CNS-regulated reflex modulates at least one of respiratory bursting, upper airway function, and chest wall muscle function in the sleeping patient.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
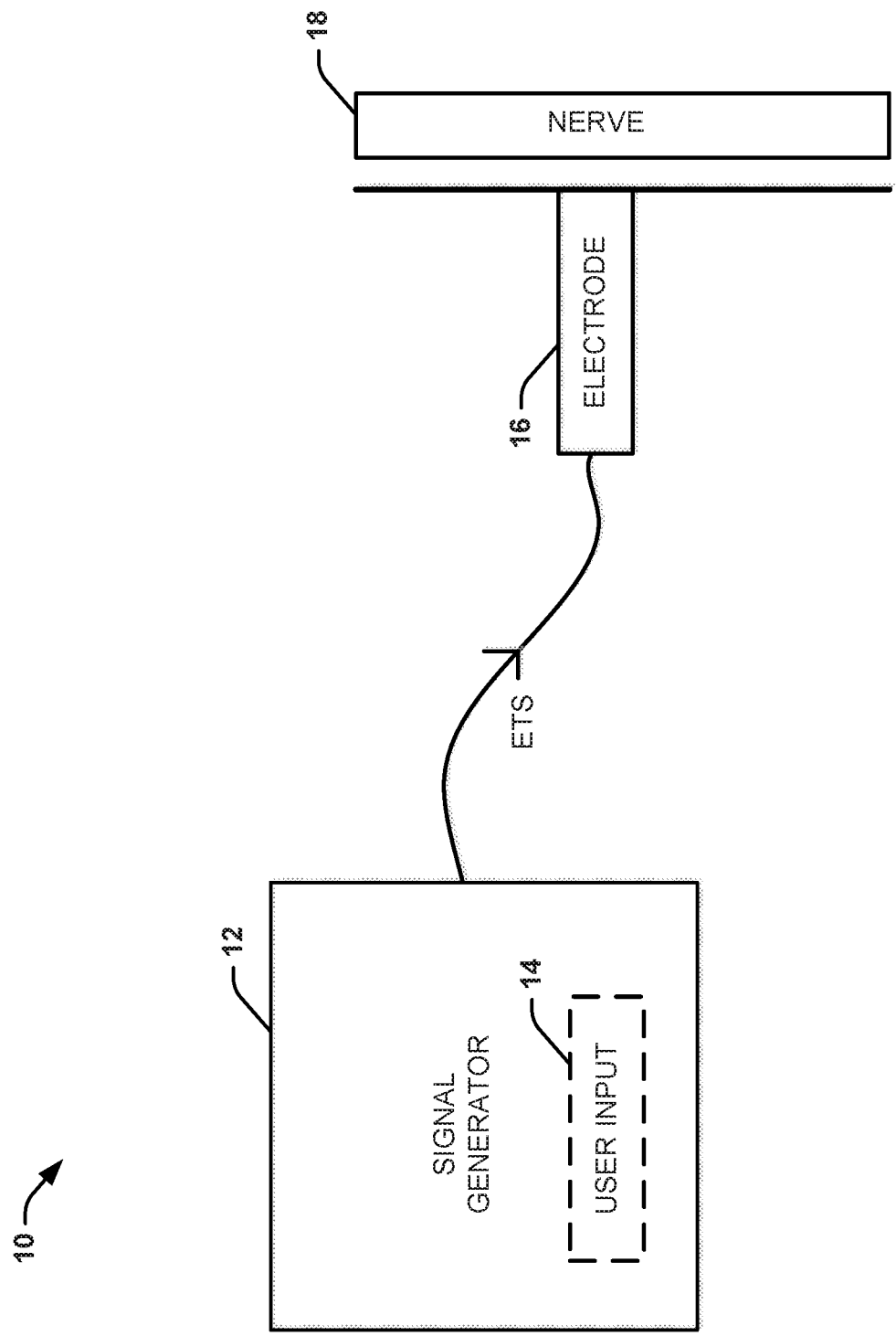
FIG. 1 is a block diagram showing a system that delivers an electrical stimulation to selectively activate endogenous reflex responses associated with airway function to ensure airway patency during sleep, according to an aspect of the present disclosure.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

When an element or structure is referred to herein as being "on," "engaged to," "connected to," "attached to", or "coupled to" another element or structure, it may be directly on, engaged, connected or coupled to the other element or structure, or intervening elements or structures may be present. In contrast, when an element is referred to as being "directly on," "directly engaged to," "directly connected to," or "directly coupled to" another element or structure, there may be no intervening elements or structures present. Other words used to describe the relationship between elements should be interpreted in a like fashion (e.g., "between" versus "directly between," "adjacent" versus "directly adjacent," etc.).

As used herein, the term "airway" can generally refer to the upper airway, which includes the nose, nasal passages, paranasal sinuses, the pharynx, and the portion of the larynx above the vocal cords. The upper airway can include several muscles innervated by cranial nerves (CN) V, X, IX, and/or XII. Examples of these muscles include the alae nasi, the genioglossus, and the posterior cricoarytenoid. The upper airway can also include muscles other than those activated by CN nerves (e.g., the phrenic nerve-diaphragm unit).

As used herein, the term "patency", when referring to an airway, can refer to the airway remaining open. Airway patency can be ensured by preventing airway obstruction.

As used herein, the term "sleep" can refer to a naturally-occurring condition of a patient's body characterized by a temporary loss of consciousness (complete or partial). The temporary loss of consciousness is characterized by a marked decrease in bodily movement and responsiveness to external stimuli.

As used herein, the term "endogenous" can refer to something that is naturally occurring within a patient's body.

As used herein, the term "reflex" can refer to a behavior that is mediated via one or more reflex arcs (e.g., a neural pathway that controls an action). The reflex-arc can be regulated or mediated by a portion of the central nervous system (CNS). One example of a CNS-regulated reflex is a brainstem-regulated reflex, which can be a reflex that when activated by afferent stimulation during sleep results in CN activation through a neural network ("pathway") through the brainstem. Another example of a CNS-regulated reflex is a reflex that is activated entirely within the spinal cord.

As used herein, the term "reflex response" can refer to an action (or reflexive behavior) that occurs due to the reflex. Examples of reflex responses include, but are not limited to, contraction or relaxation of upper airway muscles and/or chest wall muscles, respiratory bursting, and upper airway function.

As used herein, the term "sleep apnea" can refer to a type of sleep disorder characterized by pauses in breathing or instances of shallow or infrequent breathing during sleep. Non-limiting examples of sleep apnea can include obstructive sleep apnea (OSA) and central sleep apnea (CSA), in which upper airway patency may also be impaired.

As used herein, the terms "obstructive sleep apnea" or "OSA" can refer to a breathing disorder that occurs primarily during sleep with consequences that may persist throughout the waking hours in the form of sleepiness. OSA can be characterized by periodic collapse of the upper airway during sleep with apneas, hypopneas, or a continuous or sustained reduction in ventilation and excessive daytime sleepiness, neurocognitive defects and depression.

As used herein, the terms "central sleep apnea" or "CSA" can refer to breathing that is interrupted during sleep by a lack of respiratory effort, but is often associated with periodic collapse of the upper airway during sleep.

As used herein, the term "electrical therapy signal" can refer to an electrical signal that can be generated by a stimulation generator and applied (e.g., via an electrode) to achieve neural stimulation. In some instances, the electrical therapy signal can be a mathematical description of a change in voltage over time ("voltage-controlled") or a change in current over time ("current-controlled"). The term "electrical therapy signal" can refer to an electrical signal configured to provide a particular therapeutic result, such as treating sleep apnea to ensure airway patency.

As used herein, the terms "nerve stimulation" or "stimulation" can refer to the application of an electrical therapy signal to activate a bodily function. In some instances, the stimulation can be "direct", where the electrical therapy signal is applied to a nerve and the function results (e.g., stimulating motor neurons). In other instances, the stimulation can be "indirect", where the electrical therapy signal is applied to the nerve to trigger a reflex (e.g., stimulating an area on the skin to activate sensory nerves).

As used herein, the term "impulse" can refer to an action potential and/or a train of action potentials.

As used herein, the term "peripheral nerve" can refer to a nerve in a patient's body other than the nerves comprising the brain and spinal cord. Examples of peripheral nerves can include the sciatic nerve, the vagus nerve, and the esophageal nerve. Peripheral nerves can include afferent and efferent nerve fibers. Afferent nerve fibers can transmit an impulse from a stimulation site to the brain or spinal cord, the CNS. One example of an afferent nerve fiber is a sensory nerve fiber. Efferent nerve fibers can transmit an impulse from the brain or spinal cord (CNS) to an organ to provide a reflex response. An example of an efferent nerve fiber is a motor nerve fiber.

As used herein, the term "electrode" can refer to an electrical conductor that conducts current to a patient's body. In some instances, an electrode can refer to a "temporary" electrode that can be paced in or on the body and subsequently removed. In some instances, the temporary electrode can be removed without surgical intervention. Examples of temporary electrodes can include skin electrodes, transcutaneous electrodes, transmucosal electrodes, or intra-esophageal electrodes. In other instances, the electrode may be more permanent, such as a nerve cuff electrode or electrodes of an implantable TENS unit.

As used herein, the term "patient" can be used interchangeably with the term "subject" and refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure relates generally to airway patency and, more specifically, to systems and methods for selectively activating endogenous central nervous system (CNS)-regulated reflex responses associated with airway function to ensure airway patency during sleep. Advantageously, the present disclosure provides systems and methods for stimulating a peripheral nerve, such as the sciatic nerve, the vagus nerve, or the esophageal nerve, to activate afferent fibers that trigger a CNS-regulated reflex to activate one or more various muscles that control airway patency. For example, the CNS-regulated reflex can be a brainstem-regulated-reflex. Accordingly, by stimulating afferent fibers of a peripheral nerve of a patient, a brainstem-regulated reflex can be triggered to activate muscles that ensure airway patency in the patient. This stimulation of afferent fibers is particularly useful in patents with sleep apnea by reflexively activating muscles that ensure airway patency during sleep.

Stimulating afferent nerve fibers can provide an effective, efficient, and safe alternative to traditional hypoglossal nerve stimulation. Hypoglossal nerve stimulation provides direct stimulation of the efferent (motor) nerve fibers innervating the genioglossal muscle. The present disclosure, however, does not deliver direct stimulation to maintain airway patency. Rather, the present disclosure provides an alternative to direct hypoglossal nerve stimulation by activating certain endogenous reflexes (e.g., brainstem-regulated reflexes) associated with upper airway function via indirect stimulation. Indirect stimulation is the application of neural stimulation to activate a reflex that leads to the desired motor function (e.g., maintaining airway patency). Advantageously, indirect stimulation can be achieved with temporary electrodes, which can be easily removed after use, as compared to hypoglossal stimulation, which requires more permanent electrodes. Accordingly, reflex stimulation of the present disclosure reduces costs compared to hypoglossal nerve stimulation, as well as reduces the risk of medical complications (e.g., infection) associated with surgical implant procedures.

III. Systems

One aspect of the present disclosure can include a system 10 (FIG. 1) that delivers an electrical stimulation to selectively activate endogenous reflex responses associated with airway function to ensure airway patency during sleep. The system 10 can deliver indirect stimulation, in which a reflex is activated by the stimulation to ensure airway patency. This indirect stimulation is distinct from other types of stimulation, like hypoglossal nerve stimulation, which delivers direct stimulation. The indirect stimulation of the system 10 can lead to the reflexive stimulation of one or more efferent nerves (e.g., cranial nerves) via stimulation of an afferent nerve, while direct stimulation can directly stimulate neural tissue related to only a single cranial nerve.

The system 10 can include a signal generator 12 coupled to an electrode 16. In some instances, the signal generator 12 and the electrode 16 can be coupled or connected for signal transmission through a wired connection. In other instances, the signal generator 12 and the electrode 16 can be coupled or connected for signal transmission through a wireless connection (e.g., transmitting the electrical therapy signal (ETS) by a radio frequency signal). In still other instances, the signal generator 12 and the electrode can be coupled or connected for signal transmission through a combined wired and wireless means.

The signal generator 12 can be configured or programmed to generate an electrical therapy signal (ETS), which can be transmitted to the electrode 16. In some instances, the signal generator 12 itself can configure or program one or more parameters the electrical therapy signal (ETS). As an example, the parameters can be one or more of polarity, amplitude, strength, frequency, shape, duration, etc. The parameters can be configured or programmed based on the specific patient or a specific application, for example. In some instances, the configuration can be based (at least in part) on a user input 14. In other instances, the configuration can be based (at least in part) on a stored configuration protocol.

The electrode 16 can receive the electrical therapy signal (ETS) and apply the electrical therapy signal (ETS) to a nerve 18, such as an afferent fiber of a peripheral nerve. For example, the nerve 18 can be a sciatic nerve, a vagus nerve, an esophageal nerve, or any other nerve associated with airway patency. In some instances, the electrode 16 can include one or more temporary electrodes. The temporary electrodes can be applied in a configuration designed to stimulate one or more afferent nerve fibers of a peripheral nerve. In some instances, the temporary electrode can be removable. Examples of removable electrodes can include a skin electrode, a transcutaneous electrode, a transmucosal electrode, or an intra-esophageal electrode. In other instances, the electrode can be more permanent, such as an implantable nerve cuff electrode, one or more electrodes from an implantable TENS device, or the like.

The electrical therapy signal (ETS) can be configured or programmed to activate one or more afferent fibers within the nerve 18. The electrical therapy signal (ETS) can also be configured or programmed so that it causes minimal electrochemical damage to the patient's body or the electrode 16. For example, in some instances, the electrical therapy signal (ETS) can be a charge-balanced (or substantially charge balanced) bi-phasic signal. As another example, the electrical therapy signal (ETS) can be a monophasic signal configured so as to not cause electrochemical damage to the nerve 18. As such, the electrical therapy signal (ETS) can be configured or programmed by the signal generator 12 with a strength, a frequency, and for a time sufficient to stimulate a nerve 18 (e.g., to activate afferent fibers of the nerve). In some instances, the electrical therapy signal (ETS) can be configured or programmed with a frequency parameter from 1 Hz to 1000 Hz and a duration parameter from 0.01 ms to 100 ms. In other instances, the electrical therapy signal (ETS) can be configured or programmed with a frequency parameter from 3 Hz to 500 Hz and a duration parameter from 0.05 ms to 50 ms. In still further instances, the electrical therapy signal (ETS) can be configured or programmed with a frequency parameter from 5 Hz to 100 Hz and a duration parameter from 0.1 ms to 10 ms.

Figure 2:
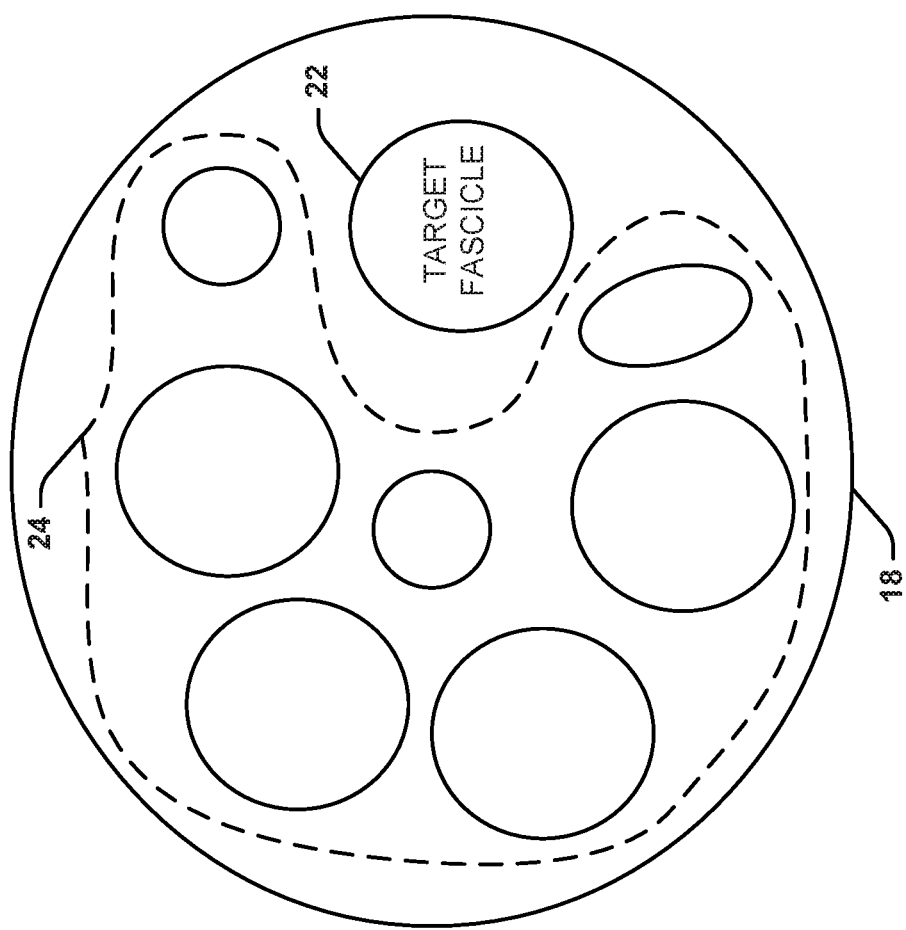
FIG. 2 is a schematic diagram of a target fascicle of the electrical stimulation of the system in FIG. 1.

The electrode 16 can apply the electrical therapy signal (ETS) to the nerve 18 to selectively activate an endogenous CNS-regulated reflex. Accordingly, the electrical therapy signal (ETS) can be configured or programmed to stimulate afferent fibers, while not substantially stimulating efferent fibers (or so that there is a minimal motor response from direct stimulation). In some instances, this selective stimulation can be accomplished by identifying a target fascicle 22 of the nerve 18 that includes a majority of afferent fibers. As shown in FIG. 2, the electrical therapy signal (ETS) can be configured or programmed to activate a target fascicle 22 within the nerve 18, while not activating the other fascicles 24. The electrical therapy signal (ETS) can include configurable parameters, including polarity, amplitude, strength, frequency, shape, duration, etc., which can be configured based on the target fascicle 22.

The afferent nerve fiber(s) in the target fascicle 22 can activate a target within the CNS to selectively activate one or more endogenous CNS-regulated reflex, which triggers a reflex response within one or more muscles muscles, thereby ensuring airway patency. In some instances, CNS-regulated reflex can include a single reflex arc (e.g., like a spinal cord reflex). In other instances, the CNS=regulated reflex can include multiple reflex arcs (e.g., like a brainstem reflex, as shown, for example, in FIG. 3).

Figure 3:
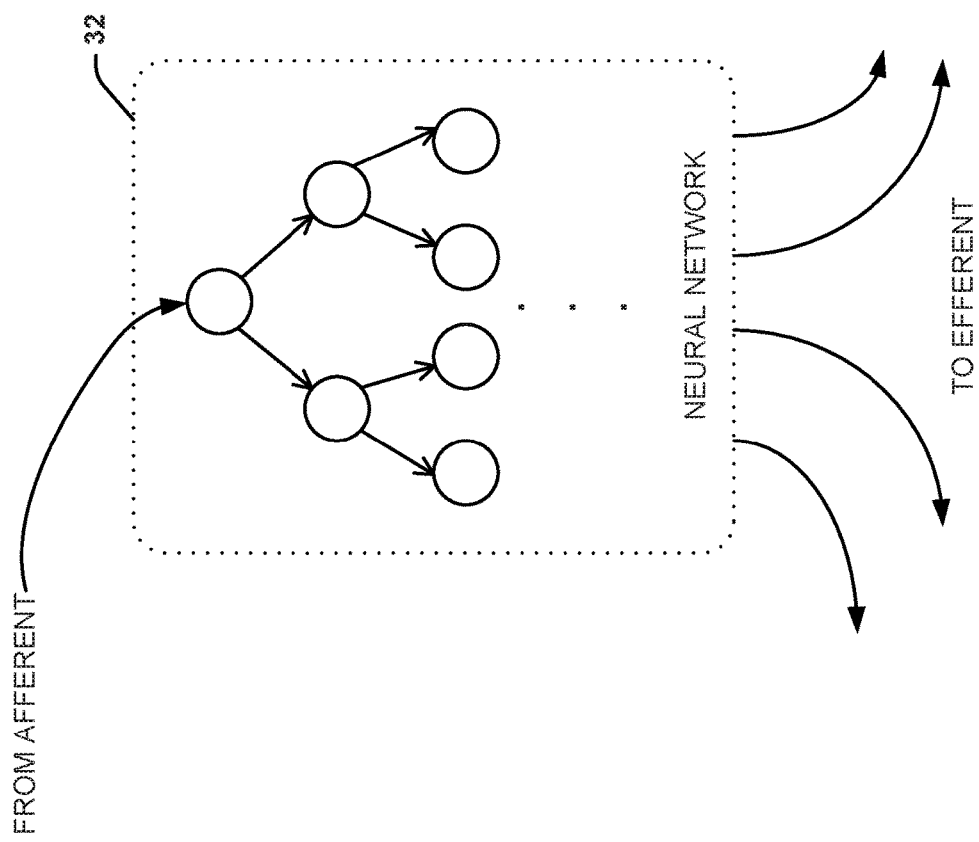
FIG. 3 is a schematic diagram illustrating an example of a neural network that can be triggered by the electrical stimulation of the system in FIG. 1.

In some instances, the endogenous reflex can be a brainstem-regulated reflex. As shown in FIG. 3, the activated target in the brainstem can activate a neural network 32 within the brainstem, which can activate cranial nerves. The cranial nerves can be one or more of cranial nerve (CN) V, X, IX, and XII. The activated cranial nerves can cause a reflex response in CN associated muscles that are related to airway patency. However, it will be understood that other efferent nerves can be reflexively activated by other CNS-regulated reflexes.

The muscles can engage in a reflexive behavior that contributes to ensuring the patency of the patient's airway during sleep. For example, the patency of the patient's airway during sleep can mimic the patency of the patient's airway when awake. For example, the reflexive behavior can include respiratory bursting, upper airway function, and/or chest wall muscle function. However, the reflexive behavior can be any behavior that reduces the impedance in the airway and/or ensures airway patency during sleep. Additionally, after stimulation, the muscles can remain active and only gradually return to their natural state, in which the airway loses patency.

IV. Methods

Another aspect of the present disclosure can include a method 40 (FIG. 4) for selectively activating endogenous reflex responses associated with airway function to ensure airway patency during sleep. In some instances, the method 40 can be performed using the system 10 (FIG. 1), which includes a signal generator 12 and an electrode 16 to apply an electrical therapy signal (ETS) to activate at least one afferent fiber in a nerve. The method 50 (FIG. 5) shows an example method 50 for the selective activation of the endogenous reflex responses of the method in FIG. 4.

Figure 6:
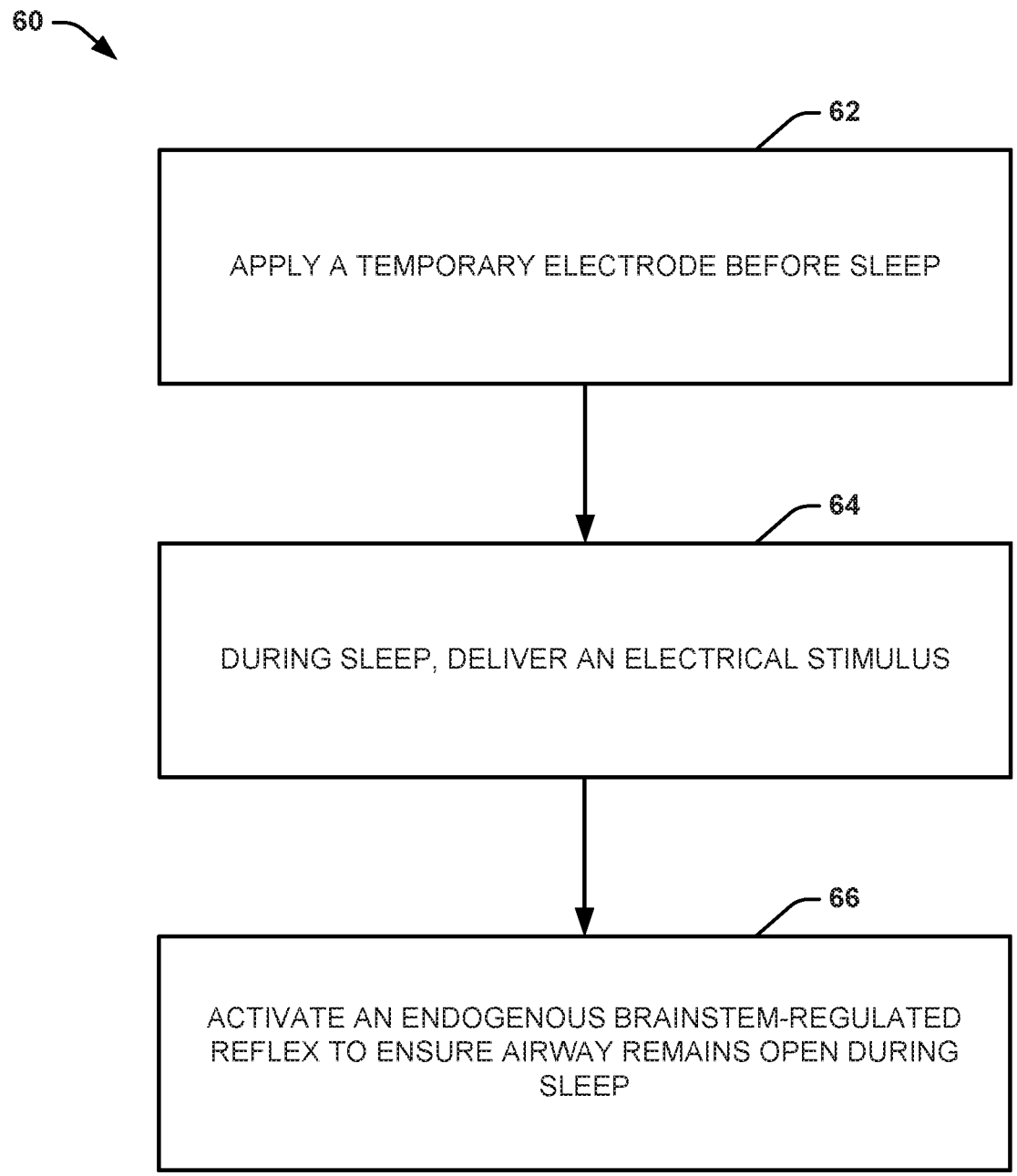
FIG. 6 is a process flow diagram illustrating a method for treating a patient with sleep apnea to ensure airway patency, according to another aspect of the present disclosure.

According to another aspect of the present disclosure, FIG. 6 illustrates a method 60 that can be used for treating a patient with sleep apnea to ensure airway patency. For example, the method 60 can be administered to a patient in need of treatment (e.g., suffering from sleep apnea) to ensure airway patency when sleeping. The method 60 can activate a brainstem-regulated reflex that modules one or more airway functions (e.g., respiratory bursting, upper airway function, and/or chest wall muscle function). For example, certain upper airway muscles and/or chest wall muscles can be reflexively activated by application of the electrical therapy signal (ETS) to treat obstructive sleep apnea (OSA) to ensure airway patency. In another example, respiratory bursting can be reflexively modulated by application of the electrical therapy signal (ETS) to restore respiratory rate and/or respiratory rhythm and thereby treat CSA by ensuring airway patency.

The methods 40-60 are illustrated as process flow diagrams with flowchart illustrations. For purposes of simplicity, the methods 40-60 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 40-60.

Figure 4:
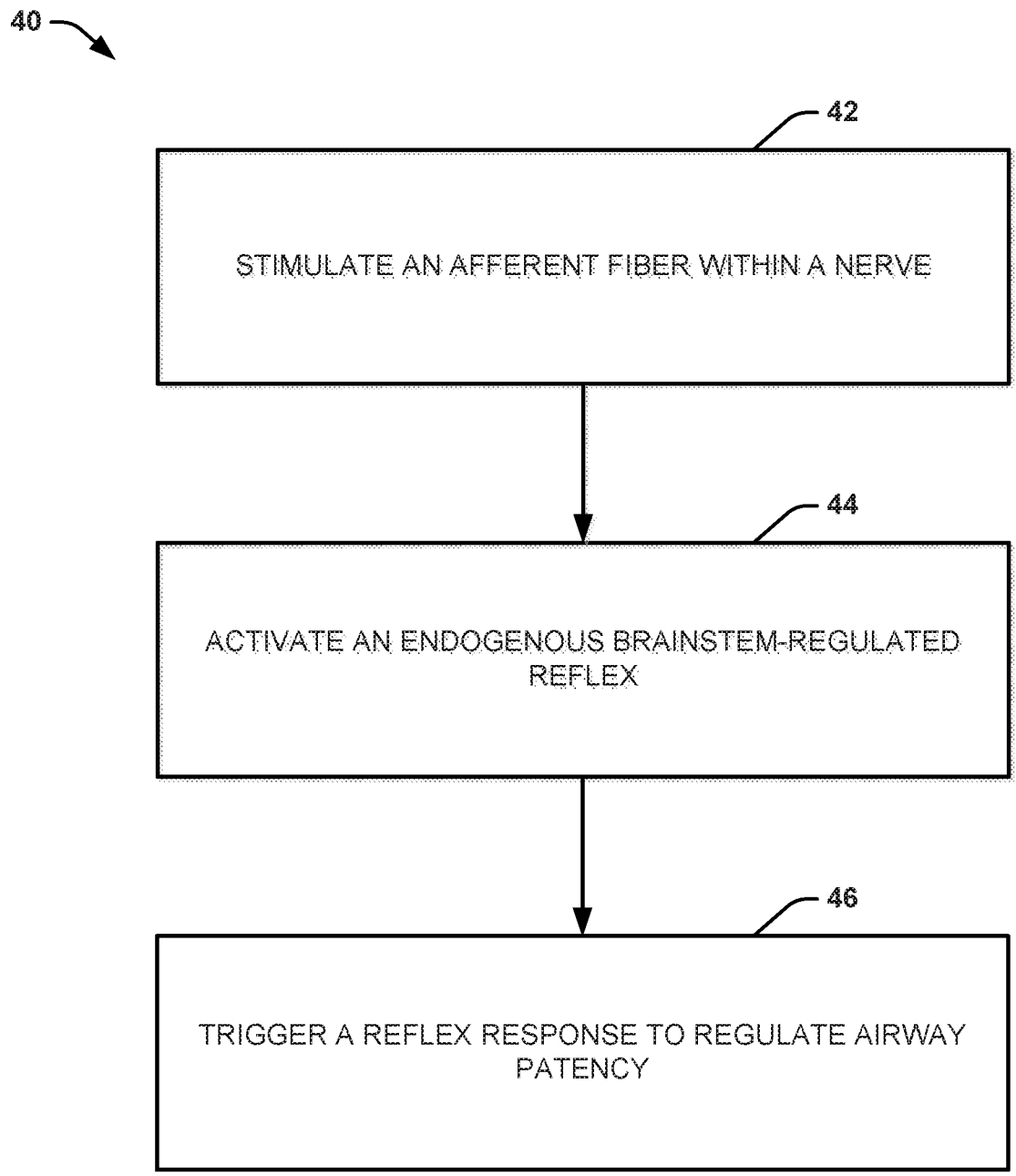
FIG. 4 is a process flow diagram illustrating a method for selectively activating endogenous reflex responses associated with airway function to ensure airway patency during sleep, according to another aspect of the present disclosure.

Referring now to FIG. 4, illustrated is a method 40 for selectively activating endogenous reflex responses associated with airway function to ensure airway patency during sleep. In other words, the method 40 can be applied when a patient is sleeping to ensure airway patency in the sleeping patient. The method 40, in some instances, can ensure airway patency by reducing a flow resistance in the sleeping patient, mimicking conditions when the patient is awake.

At 42, an afferent nerve fiber within a nerve 18 (e.g., a peripheral nerve) can be stimulated. For example, the stimulation can be applied as an electrical therapy signal (ETS) configured by a signal generator 12 and applied by an electrode 16 (e.g., a temporary electrode or a more permanent electrode) to the nerve 18. For example, the nerve 18 can be the sciatic nerve, the vagus nerve, or the esophageal nerve. One or more parameters (e.g., polarity, amplitude, strength, frequency, shape, duration, etc.) of the ETS can be configured to stimulate fibers within a target fascicle 22 of the nerve 18. For example, the target fascicle 22 can include mostly afferent fibers. However, it will be understood that the parameters can be configured to activate one or more afferent fibers in one or more fascicles in the nerve 18, while not substantially activating efferent fibers in the nerve 18.

At 44, an endogenous brainstem-regulated reflex can be activated due to the electrical therapy signal (ETS). It will be understood that other CNS-regulated reflexes can be activated (additionally or alternatively) due to the electrical therapy signal (ETS). For example, the afferent fiber activated by the electrical therapy signal (ETS) ultimately facilitates transmission of a signal to the brainstem. A neural network 32 can be activated in the brainstem, so that a plurality of efferent signals is generated through cranial nerves (CN). The efferent signals activate muscles associated with airway patency to trigger a reflex response. At 46, the reflex response can be triggered to regulate airway patency. The reflex response can regulate airway patency to ensure that the patient's airway remains open during sleep. For example, the reflex response can modulate respiratory bursting, upper airway function, and chest wall muscle function in the sleeping patient.

Figure 5:
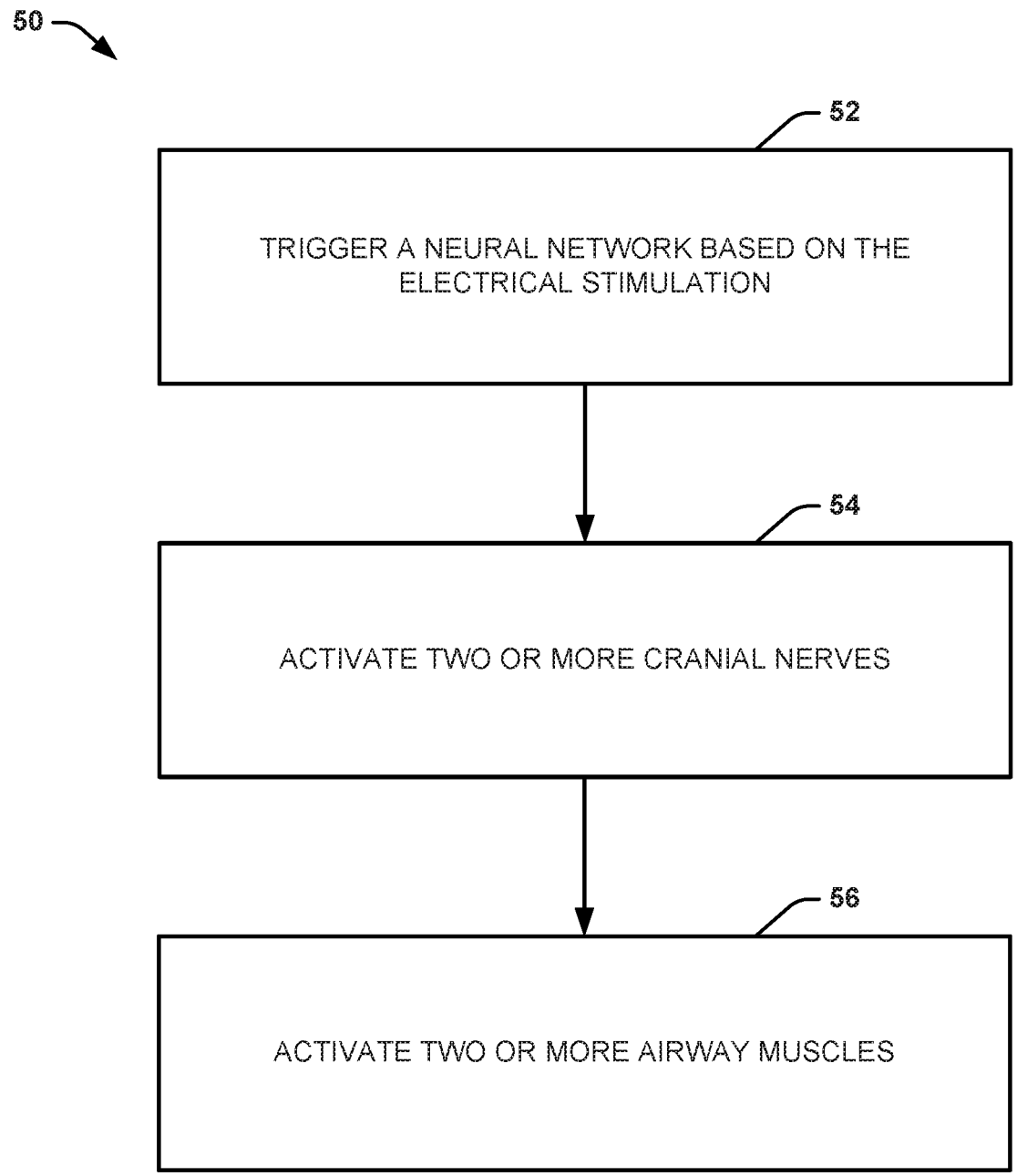
FIG. 5 is a process flow diagram illustrating the selective activation of the endogenous reflex responses of the method in FIG. 4.

FIG. 5 is illustrates a method 50 for selective activation of the endogenous reflex responses. The method 50 can be accomplished within the method 40, as described above. At 52, a neural network can be triggered based on the electrical therapy signal (ETS). For example, at least a portion of the afferent nerve fiber(s) in the nerve 18 can be selectively activated. Due to the activation, a signal can be transmitted to a portion of the brainstem. The portion of the brainstem become activated and, in turn, activates other areas of the brainstem, which can activate still other areas of the brainstem to create an activated neural network. At 54, cranial nerves (CNs) can be activated by the activated CNS neural network. For example, the activated cranial nerves (CN) can include CN V, X, IX, and XII. At 56, the activated cranial nerves can, in turn, activate airway muscles. Examples of such airway muscles include, but are not limited to, the alae nasi, the genioglossus, and the posterior cricoarytenoid. The activation of the airway muscles can ensure airway patency.

Referring now to FIG. 6, illustrated is a method 60 for treating a patient with sleep apnea to ensure airway patency, according to another aspect of the present disclosure. The method 60 can ensure airway patency of the patient during sleep, substantially mimicking airway patency when the patient is awake. For example, the sleep apnea can be obstructive sleep apnea (OSA) or central sleep apnea (CSA). At 62, a temporary electrode configuration can be applied to a patient before sleep. The temporary electrode configuration can be coupled or connected to a stimulator. For example, the temporary electrode configuration can include a skin electrode, a transcutaneous electrode, a transmucosal electrode, or an intra-esophageal electrode. After the patient falls asleep, an electrical therapy signal (ETS) can be delivered to the patient through the electrode configuration. For example, the electrical therapy signal (ETS) can be configured to activate one or more afferent fibers in a nerve 18. The activated afferent fibers can activate an endogenous brainstem-regulated reflex. At 66, based on the electrical therapy signal (ETS), an endogenous brainstem-regulated reflex can be activated to ensure that the patient's airway remains open during sleep. By ensuring airway patency, the application of the electrical therapy signal (ETS) can treat sleep apnea. For example, a response to the endogenous brainstem-regulated reflex can modulate at least one of respiratory bursting, upper airway function, and chest wall muscle function in the sleeping patient.

From the above description, those skilled in the art will perceive improvements, changes and modifications. Such improvements, changes and modifications are within the skill of one in the art and are intended to be covered by the appended claims.

What is claimed is:

1. A method comprising:
applying an electrical stimulus through an electrode to stimulate an afferent nerve fiber within a sciatic nerve or a vagus nerve while a patient is sleeping;
activating an endogenous central nervous system (CNS)-regulated reflex response that modulates respiratory bursting in the sleeping patient based on the stimulation of the afferent nerve fiber; and
regulating airway patency in the sleeping patient based on an endogenous CNS-regulated reflex response.

2. The method of claim 1, wherein the electrode is a temporary electrode that is removable after the patient wakes up.

3. The method of claim 2, wherein the electrode is a skin electrode, a transcutaneous electrode, a transmucosal electrode, or an intra-esophageal electrode.

4. The method of claim 1, wherein the airway patency is regulated to ensure that the patient's airway remains open during sleep.

5. The method of claim 4, wherein the patient suffers from obstructive sleep apnea or central sleep apnea.

6. The method of claim 1, wherein the afferent nerve fiber is located within a nerve that relays peripheral information to the CNS to trigger a reflex that results in the endogenous CNS-regulated reflex response.

7. The method of claim 1, wherein the electrical stimulus comprises a strength parameter, a frequency parameter, and a duration parameter sufficient to activate the endogenous CNS-regulated reflex response.

8. The method of claim 7, wherein the frequency parameter is from 5 Hz to 100 Hz and the duration parameter is from 0.1 ms to 10 ms.

9. The method of claim 1, wherein a flow resistance in the sleeping patient is reduced by the CNS-regulated reflex response, mimicking conditions when the patient is awake.

10. A system comprising:
a signal generator programmed to generate an electrical therapy signal comprising a strength parameter, a frequency parameter, and a duration parameter sufficient to activate an endogenous CNS-regulated reflex response; and
an electrode, coupled to the signal generator, to apply the electrical therapy signal to an afferent nerve fiber of a peripheral nerve of a sleeping patient to activate the endogenous CNS-regulated reflex response to regulate airway patency in the sleeping patient, wherein the peripheral nerve is a sciatic nerve or a vagus nerve, and wherein a response to the endogenous CNS-regulated reflex modulates respiratory bursting in the sleeping patient.

11. The system of claim 10, wherein the electrode is a skin electrode, a transcutaneous electrode, a transmucosal electrode, or an intra-esophageal electrode.

12. The system of claim 10, wherein the endogenous CNS-regulated reflex response regulates at least one efferent nerve-muscle unit that opens at least a portion of the airway of the sleeping patient to contribute to the airway patency.

13. A method comprising:
applying a temporary electrode configuration to a patient before sleep, wherein the temporary electrode configuration is coupled to a stimulator;
during sleep, delivering an electrical stimulus through the temporary electrode configuration to stimulate an afferent nerve fiber of a sciatic nerve or a vagus nerve; and
based on the electrical stimulus, activating an endogenous brainstem-regulated reflex to ensure that the patient's airway remains open during sleep;
wherein a response to the endogenous CNS-regulated reflex modulates respiratory bursting in the sleeping patient.

14. The method of claim 13, wherein the endogenous CNS-related reflex regulates at least one of a CN V muscle, X muscle, IX muscle, and XII muscle.

15. The method of claim 13, wherein the electrode configuration comprises a skin electrode, a transcutaneous electrode, a transmucosal electrode, or an intra-esophageal electrode.

16. The method of claim 13, wherein the sleeping patient suffers from obstructive sleep apnea or central sleep apnea.

* * * * *